United States Patent [19]

Rose

[11] Patent Number: 5,030,212
[45] Date of Patent: Jul. 9, 1991

[54] PUNCTURE GUARD FOR NEEDLE ADMINISTRATION SET

[76] Inventor: Peter J. Rose, 18 Shady Glen Ct., New Rochelle, N.Y. 10805

[21] Appl. No.: 559,910

[22] Filed: Jul. 30, 1990

[51] Int. Cl.⁵ .............................................. A61M 5/00
[52] U.S. Cl. ...................................... 604/263; 604/192
[58] Field of Search ............... 604/192, 110, 263, 198, 604/162, 167

[56] References Cited

U.S. PATENT DOCUMENTS

| | | | |
|---|---|---|---|
| 3,900,026 | 8/1975 | Wagner. | |
| 3,901,226 | 8/1975 | Scardenzan. | |
| 4,139,010 | 2/1979 | Dykstra | 604/263 |
| 4,170,993 | 10/1979 | Alvarez | 604/263 |
| 4,500,312 | 2/1985 | McFarlane | 604/263 |
| 4,631,058 | 12/1986 | Raines | 604/263 |
| 4,743,233 | 5/1988 | Schneider | 604/192 |
| 4,775,367 | 10/1988 | Schmidt | 604/192 |
| 4,781,692 | 11/1988 | Jagger et al. | 604/164 |
| 4,830,282 | 4/1989 | Hogan | 604/263 |
| 4,842,586 | 6/1989 | Hogan | 604/192 |
| 4,846,804 | 7/1989 | Davis et al. | 604/263 |
| 4,850,961 | 7/1989 | Wanderer et al. | 604/263 |
| 4,935,011 | 6/1990 | Hogan | 604/263 |
| 4,941,881 | 7/1990 | Masters et al. | 604/162 |

*Primary Examiner*—C. Fred Rosenbaum
*Assistant Examiner*—Sharon Finkel
*Attorney, Agent, or Firm*—Natter & Natter

[57] ABSTRACT

A puncture guard for a needle administration set having a needle assembly with a pair of flexible transverse wings includes a cylindrical sleeve which is outwardly flared at one end. One or more transverse openings are provided through the sleeve adjacent the opposite end. The administration set tubing is threaded axially through the sleeve with the flared end facing the needle assembly. Upon removal of the needle from the patient, the sleeve is grasped and the tubing is pulled so that the needle assembly wings engage the flared end of the sleeve. Further pulling of the tubing causes the wings to bend as the needle assembly is pulled into the sleeve. Rotation of the sleeve or tubing relative to each other when the wings are registered with the transverse opening causes the wings to spring outwardly through the transverse opening, locking the needle assembly within the sleeve with the tip of the needle safely confined.

21 Claims, 2 Drawing Sheets

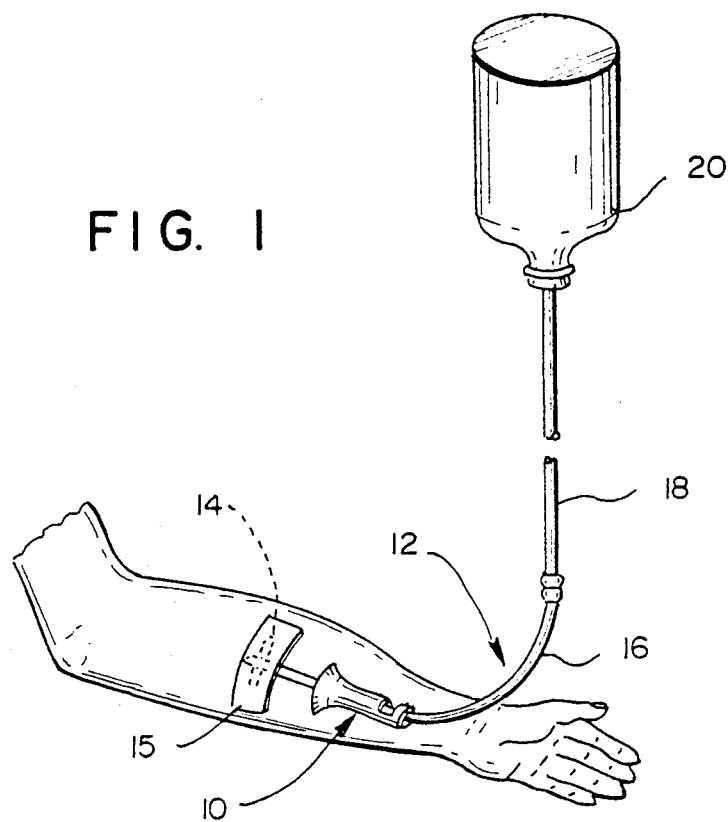
FIG. 1
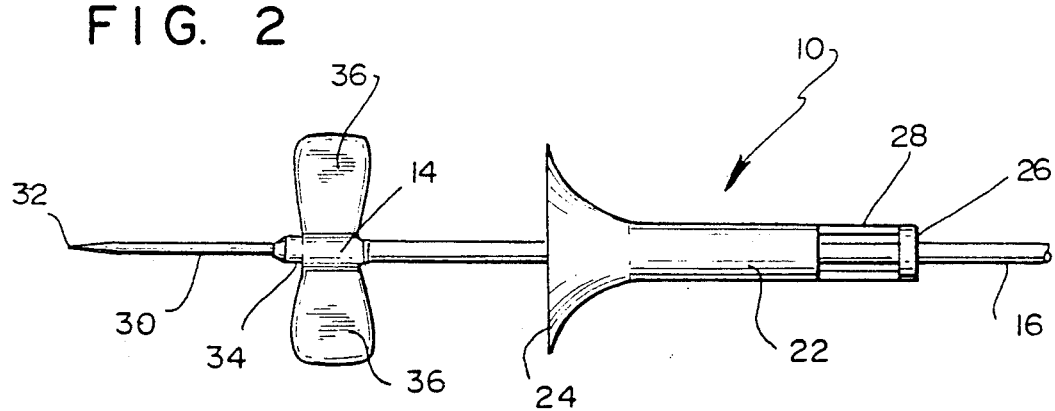
FIG. 2
FIG. 4
FIG. 3

PUNCTURE GUARD FOR NEEDLE ADMINISTRATION SET

BACKGROUND OF THE INVENTION

1. Field of the Invention

This invention relates generally to needle administration sets for medical procedures involving the infusion or drainage of fluids and more particularly to safety guards for preventing inadvertent punctures from needles after completion of the medical procedure.

2. Background History

Medical treatments and procedures employing infusion and/or extraction of fluids through the use of needle administration sets have been common, routine procedures for many years. Such procedures are employed not only in conventional medical facilities such as hospitals, nursing homes and health care facilities but, in addition, it has become a fairly common practice for patients and family members in home environments.

Packaged sterilized administration sets generally included a sealed tubing length, capped at one end, and having a needle assembly at the other end. The needle assembly included a quill tipped hollow metal needle joined to a coaxial hollow thermoplastic base. The thermoplastic base included an integrally molded pair of transverse flexible wings. The wings were normally biased outwardly and generally coplanar.

In order to facilitate insertion of the needle tip into the patient, the wings were grasped and bent to face one another between the thumb and forefinger. Thereafter, the wings naturally sprung back to a coplanar orientation and were taped or secured to the user's skin to maintain the inserted needle assembly in position.

After the appropriate treatment of fluid infusion and/or drainage had been completed, the needle was withdrawn from the patient. Prior to disposal, it was necessary to recap the needle to prevent inadvertent punctures or needle sticks. Inadvertent needle punctures from used needle assemblies have been known to result in the contraction of highly contagious fatal diseases including the dreaded acquired immune deficiency syndrome.

The apparently simple task of recapping a needle has itself resulted in inadvertent punctures since the sharp tip of the needle had a tendency to contact the hand of a person attempting to recap the needle, especially if the needle was not positioned precisely coaxial with a hollow bore of a cap. This resulted from the fact that the user's hand, holding the cap, was moving in a direction toward the pointed tip of the needle.

One approach toward providing a safety sheath for needles of an administration set was shown in U.S. Pat. No. 4,820,282. This patent disclosed a sheath having generally planar base. Spaced from the base and extending parallel to the base was an upper wall. In use, the sheath was to be precisely aligned with the needle assembly such that the wings of the needle assembly were registered with the space between the base and the upper wall. Thereafter, the sheath was moved relative to the needle assembly, toward the tip of the needle. The sheath included a pair of retaining springs which extended into the space and the retaining springs were to deflect to permit the wings to pass and then snap back into the space behind the wings to lock the needle assembly within the sheath.

The device of U.S. Pat. No. 4,820,282 suffered from several inherent disadvantages, among them was the fact that the wings of the needle assembly had to be precisely aligned and registered with the space between the base and the upper wall. A further potential for difficulty in usage was presented by the springs which extended into the space. The springs had the potential for preventing the wings of the needle assembly from passing, and then locking behind the wings. This, of course, was a function of the material of which the needle assembly wings was fabricated and the force required to move the springs out of the path of the wings. Generally, the wings were fabricated of relatively soft, yieldable thermoplastic such that they may be readily bent and grasped for insertion of the needle.

SUMMARY OF THE INVENTION

In compendium, the present invention comprises a puncture guard for a needle administration set which is positioned over the tubing of the administration set and is utilized to prevent inadvertent punctures from a used needle.

The puncture guard includes a cylindrical sleeve having an outwardly flared end facing a needle assembly of the administration set. Adjacent the opposite end of the sleeve, a transverse opening is provided.

After the medical procedure has been completed and the needle is removed from the patient, the cylindrical sleeve is grasped and the administration tubing is pulled relative to the sleeve so that the needle assembly moves toward the flared end of the sleeve.

The flexible transverse wings of the needle assembly engage the flared opening which provides a camming surface to bend the wings close to the body of the needle assembly. Further movement of the tubing relative to the sleeve results in the needle assembly being drawn into the sleeve.

When the wings are registered with the transverse opening, the tubing is rotated relative to the sleeve until both wings spring outwardly through the opening and regain their normal position, thus locking the needle assembly within the sleeve and with the tip of the needle inaccessibly positioned within the sleeve.

From the foregoing summary, it will be appreciated that it is a consideration of the present invention to provide a puncture guard of the general character described for a needle administration set which is not subject to the disadvantages of the background history aforementioned.

A feature of the present invention is to provide a puncture guard of the general character described for a needle administration set which is simple to use.

It is an aspect of the present invention to provide a puncture guard of the general character described for a needle administration set which is low in cost and may be fabricated utilizing mass production techniques.

A further aspect of the present invention is to provide a puncture guard of the general character described for a needle administration set which is well suited for use with conventional butterfly type needle assemblies from a wide variety of sources.

Another feature of the present invention is to provide a puncture guard of the general character described for a needle administration set which is capable of rendering a needle tip inaccessible without requiring relative movement of one's hand in a direction toward the tip of the needle.

To provide a puncture guard of the general character described for a needle administration set which lockingly engages needle assembly without having moving parts is yet a further consideration of the present invention.

Other aspects, features and considerations in part will be obvious and in part will be pointed out hereinafter.

With these ends in view, the invention finds embodiment in certain arrangements of parts, combinations of elements and series of steps by which the aforesaid aspects, features and considerations and certain other aspects, features and considerations are attained, all with reference to the accompanying drawings and the scope of which is more particularly pointed out and indicated in the appended claims.

BRIEF DESCRIPTION OF THE DRAWINGS

In the accompanying drawings in which are shown some of the various possible exemplary embodiments of the invention, FIG. 1 is a perspective illustration of an intravenous administration procedure and showing a puncture guard constructed in accordance with and embodying the invention positioned over tubing of the intravenous administration set and spaced from a needle assembly of the administration set;

FIG. 2 is an enlarged scale top plan view of the needle assembly, tubing and the puncture guard with the needle assembly shown retracted from the patient after completion a medical procedure; the puncture guard is illustrated having a cylindrical sleeve and an outwardly flared end facing the needle assembly;

FIG. 3 is a side elevational view of the puncture guard and showing the needle assembly being pulled into the puncture guard;

FIG. 4 is an enlarged scale sectional view through the puncture guard and the needle assembly, the same being taken substantially along the line 4—4 of FIG. 3 and showing a pair of flexible transverse wings of the needle assembly bent within and confined by the sleeve;

DESCRIPTION OF THE PREFERRED EMBODIMENTS

Figure 5:
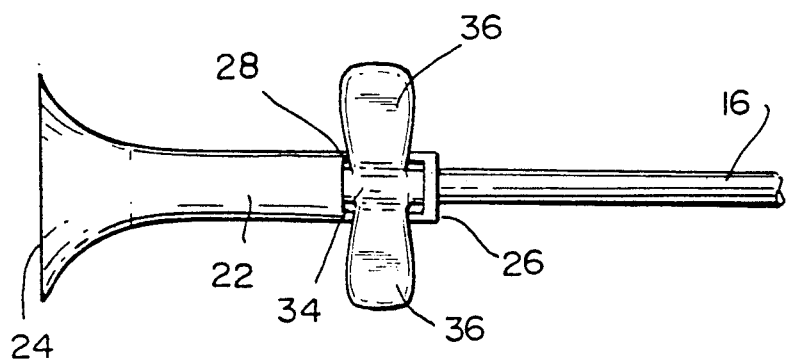
FIG. 5 is a top plan view of the puncture guard and the needle assembly with the needle assembly being pulled further into the puncture guard and with the wings extending through a transverse opening in the sleeve and locking the needle assembly within the puncture guard.

The puncture guard of the present invention is particularly well suited for utilization in conjunction with needle administration sets. The term administration sets, as employed herein, refers to a set comprising a needle assembly and a length of tubing utilized for any number of medical procedures such as the infusion of fluids into a patient, the draining of fluids from a patient or for fluid transfer procedures such as dialysis.

As will be described in detail hereinafter, the puncture guard of the present invention is particularly configured for utilization in conjunction with butterfly type needle assemblies, that is needle assemblies comprising a needle base having a pair of flexible transverse wings which are utilized for insertion of the needle into the patient and, subsequently, as a base for securing the needle assembly to the patient during the medical procedure. The present invention is configured to utilize the butterfly wings for locking the needle assembly in a cavity, with the tip of the needle inaccessible to inadvertent contact.

Referring now in detail to the drawings, the reference numeral 10 denotes generally a puncture guard in accordance with and embodying the invention and adapted for use with an administration set, denoted generally by the reference numeral 12. The administration set 12 includes a needle assembly 14 connected to a length of tubing 16. By way of example, in some medical procedures, the tubing 16 may have its end connected to a further length of tubing 18 which in turn is connected to a fluid supply 20. Conventional flow control and monitoring apparatus (not shown) is generally provided in the flow path of the tubing 18. After the needle has been inserted in the patient, the needle assembly may be secured in position against the patient's skin by adhesive tape 15.

Referring now to FIG. 2 which illustrates the puncture guard 10 and needle assembly in plan configuration, it should be noted that the puncture guard 10 includes an elongate cylindrical sleeve 22 having an axial bore, passageway or cavity. The sleeve 22 includes an outwardly flared end 24 facing the needle assembly 14. Adjacent an opposite end 26 of the sleeve, a transverse opening 28 to the bore, passageway or cavity is provided.

The puncture guard 10 may be molded in one piece by, for example, injection molding, and is fabricated of any conventional low cost thermoplastic such as polyvinyl chloride, polyethylene, acrylonitrile butadiene styrene, etc. need not be subject to sterilization for employment in conjunction with its intended function.

The needle assembly 14, includes a hollow metal, preferably stainless steel, needle 30 having a pointed quill tip 32 at one end. Coaxially positioned at the opposite end of the needle 30 is a molded plastic, generally cylindrical base 34. A pair of flexible wings 36 are joined to the base each by a unitary living hinge. Such structure is generally known, because of the transverse wings, as a "butterfly" needle assembly.

In accordance with the invention, the outwardly flared end 24 of the puncture guard 10 functions as a camming surface when it engages the edges of the wings 36 to bend the wings and permit the needle assembly to pass into a bore of the sleeve 22.

After the medical procedure has been completed and the needle 30 has been withdrawn from the patient's arm, it is imperative to quickly render the tip 32 of the needle inaccessible to persons that may come in contact with the used administration set 12.

In accordance with the invention, and with reference to the orientation of components as depicted in FIG. 2, the puncture guard 10 is grasped by one hand of the doctor, nurse or medical technician, for example, the left hand, with the thumb and forefinger grasping the sleeve 22. The user's right hand grasps the tubing 16 to the right of the end 26 of the sleeve 22. Thereafter, the tubing 16 is pulled toward the right, while the puncture guard 10 is pulled toward the left or held stationary. The needle assembly 14 moves toward the outwardly flared end 24 of the puncture guard 10.

Upon engagement of the edges of the wings 36 and the flared surface of the puncture guard, the outwardly flared surface functions as a cam to cause the wings to bend and coil radially inwardly towards the base 34 of the needle assembly, thus permitting the needle assembly 14 to be drawn into the sleeve 22 to an intermediate position, for example, the position illustrated in the elevational view of FIG. 3. The bending and coiling of the wings 36 may be facilitated by rotation of the sleeve relative to the tubing and needle assembly.

It should be noted from the sectional view of FIG. 4, that the wings 36 are confined to be concentric with and engage the interior surface or bore of the sleeve 22. As the tubing is pulled further toward the right, relative to the puncture guard 10, the wings 36 eventually register with the transverse opening 28 and at least one of the wings 36 should spring radially outwardly through the opening 28. Thereafter, the sleeve is rotated relative to the tubing and needle assembly 14 until the second wing 36 accesses the transverse opening 28 and springs radially outwardly to the position illustrated in FIGS. 5, 6 and 7.

Figure 6:
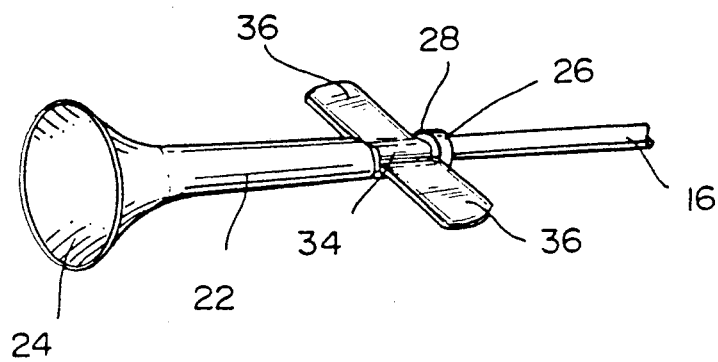
FIG. 6 is a perspective illustration of the puncture guard and needle assembly in the position illustrated in FIG. 5.
Figure 7:
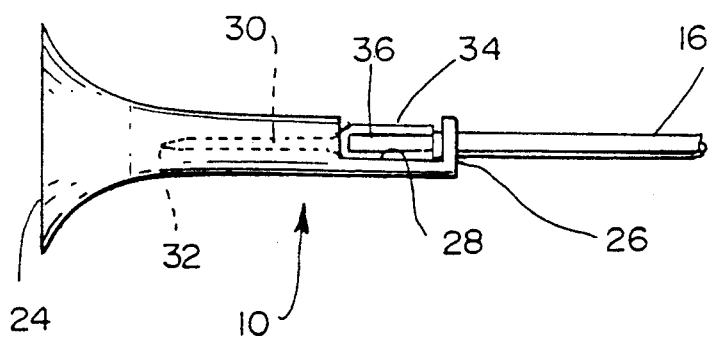
FIG. 7 is a side elevational view of the puncture guard and needle assembly in the position indicated in FIGS. 5 and 6.

In the positions illustrated in FIGS. 5, 6 and 7, the wings, extend radially through the transverse opening 28 and prevent further relative axial movement between the needle assembly 14 or tubing 16 and the puncture guard 10. As illustrated in FIG. 7, the needle 30 itself, as well as its tip 32, are inaccessibly retained within the bore of the sleeve 22 and as such, the needle tip cannot inadvertently puncture a person who comes in contact with the used administration set 12.

Figure 8:
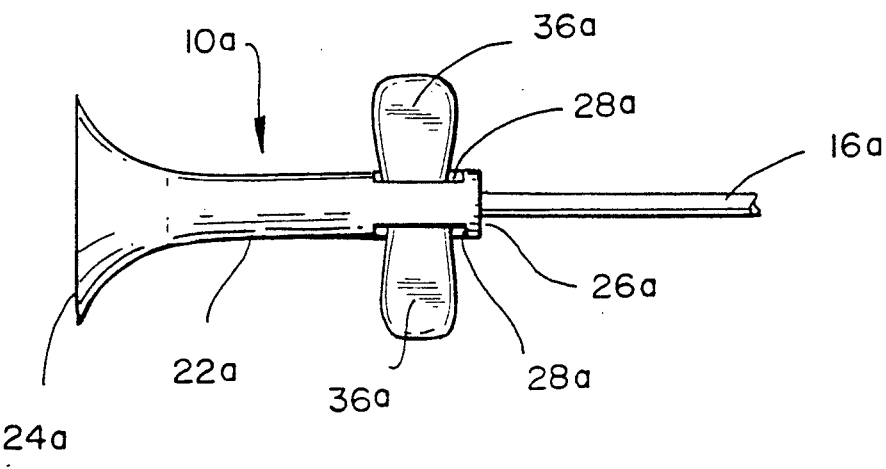
FIG. 8 is an illustration of an alternate embodiment of the puncture guard wherein a pair of transverse openings is provided through the sleeve and showing one of the wings of the needle assembly projecting through each of the transverse openings to lock the needle assembly within the puncture guard.

In FIG. 8, an alternate embodiment of the invention is disclosed wherein like numerals are employed to denote like components of the previous embodiment, however, bearing the suffix "a". In this embodiment, a puncture guard 10a having a cylindrical sleeve 22a includes an outwardly flared end 24a which faces a needle assembly and an opposite end 26a through which an administration set tubing 16a extends.

The puncture guard 10a is substantially identical to the puncture guard 10 previously described, however, in lieu of a single transverse opening 28, a pair of transverse openings 28a are provided in substantially coplanar relationship.

The puncture guard 10a functions in the identical manner as the puncture guard 10 of the previous embodiment, however, a single needle assembly wing 36a extends through each of the transverse openings 28a to lock the needle assembly in position within the puncture guard 10a.

Although the needle assembly 10 has been illustrated as being carried on the tubing 16 during the medical procedure, the tubing 16 may be threaded through the sleeve 22 after completion of the medical procedure. Further, packaged administration sets may include the puncture guard carried on the tubing.

Thus it will be seen that there is provided a puncture guard for a needle administration set which achieves the various aspects, features and considerations of the present invention and which is well suited to meet the conditions of practical usage.

While the present invention has been described with reference to the disclosed embodiments thereof, it should be understood that all matter herein described and shown in the accompanying drawings is to be interpreted as illustrative and not in a limiting sense and that numerous variations upon the invention are now enabled to those skilled in the art, which variations yet reside within the scope of the present invention.

Having thus described the invention, there is claimed as new and desired to be secured by Letters Patent:

1. A puncture guard for preventing inadvertent contact with a tip of a needle of a needle administration set after completion of a medical procedure, the administration set comprising a needle assembly and a length of tubing, the needle assembly including the needle and a coaxial base, the base being connected to the needle at an end of the needle opposite the tip, the base including at least one radially projecting wing, the wing having an axial length and a radial length, the wing being radially deformable, one end of the tubing being connected to the base for liquid flow through the tubing, the base and the needle, the puncture guard comprising a body, means defining a cavity in the body, the cavity having a pair of end openings, the cavity and the end openings being dimensioned to receive a continuous portion of the tubing with the tubing passing through each of the end openings, one of the end openings facing the needle assembly, at least a portion of the cavity being defined by an interior surface which is continuous in transverse cross section and which is nondeformable relative to the wing, the continuous interior surface having a maximum dimension transverse to the longitudinal axis of the tubing which is less than the combined radial length of the wing and the transverse thickness of the base, means forming a transverse opening in the interior surface between the other end opening and the continuous interior surface, the transverse opening being dimensioned to receive the axial length of the wing therethrough, the wing being deformed to a reduced radial length when the base is in the portion of the cavity, the wing being expandable to its undeformed radial length when the wing is registered with the transverse opening, the axial distance between the tip of the needle and the wing being less than the distance between the transverse opening and the one end opening, whereby the needle will be positioned within the cavity with its tip inaccessible to inadvertent contact when the wing is registered with the transverse opening.

2. A puncture guard for preventing inadvertent contact with a tip of a needle of a needle administration set as constructed in accordance with claim 1 wherein the body is funnel shaped.

3. A puncture guard for preventing inadvertent contact with a tip of a needle of a needle administration set as constructed in accordance with claim 1 wherein the continuous interior surface portion of the cavity is circular in transverse cross section.

4. A puncture guard for preventing inadvertent contact with a tip of a needle of a needle administration set as constructed in accordance with claim 3 wherein the body of the puncture guard is configured as a cylindrical sleeve.

5. A puncture guard for preventing inadvertent contact with a tip of a needle of a needle administration set as constructed in accordance with claim 1 wherein a pair of transverse openings are provided in the interior surface between the other end opening and the portion.

6. A puncture guard for preventing inadvertent contact with a tip of a needle of a needle administration set as constructed in accordance with claim 1 further including and in combination with the administration set, the tubing extending through the cavity prior to completion of the medical procedure.

7. A puncture guard for preventing inadvertent contact with a tip of a needle of a needle administration set as constructed in accordance with claim 1, further including and in combination with the administration set, the needle assembly being received within the cavity and the wing projecting through the transverse opening and retaining the needle assembly within the cavity.

8. The combination of a puncture guard and needle administration set as constructed in accordance with claim 7 wherein the needle assembly includes a pair of wings, both wings projecting through the transverse opening.

9. The combination of a puncture guard and needle administration set as constructed in accordance with claim 7 wherein the needle assembly includes a pair of wings, the puncture guard further including a pair of transverse openings in the interior surface between the other end opening and the portion, one of the wings projecting into each of the openings whereby the needle assembly is securely retained within the cavity.

10. A puncture guard for preventing inadvertent contact with the tip of a needle of a used needle administration set as constructed in accordance with claim 1 further including means for deforming the wing to a reduced radial length to permit the wing to be drawn from the one end opening through the continuous interior surface portion of the cavity.

11. A puncture guard for preventing inadvertent contact with the tip of a needle of a used needle administration set as constructed in accordance with claim 10 wherein the means for deforming the wing includes means for providing camming engagement between the one end opening and the wing.

12. A puncture guard for preventing inadvertent contact with a tip of a needle of a used needle administration set, the administration set comprising a needle assembly and a length of tubing, the needle assembly including the needle and a coaxial base, the base being connected to the needle at an end of the needle opposite the tip, the base including at least one radially projecting wing having a radial span, one end of the tubing being connected to the base for liquid flow through the tubing, the base and the needle, the puncture guard comprising an elongate body having an axial passageway with an opening at each end, the passageway being dimensioned to receive a continuous portion of the tubing with the tubing passing through each of the openings, one of the end openings facing the needle assembly, a portion of the passageway between the openings being defined by an axial length of rigid peripherally confining interior surface which is continuous in transverse cross section and having a maximum dimension transverse to the longitudinal axis of the tubing, the maximum dimension being less than the combined radial span of the wing and the transverse thickness of the base, means for reducing the radial span of the wing to permit entry of the base and the wing into the portion of the passageway, means forming a transverse enlargement in the passageway between the other end opening and the portion, the transverse enlargement being dimensioned to accommodate the unreduced radial span of the wing the axial distance between the tip of the needle and the wing being less than the distance between the transverse enlargement and the one cavity opening, whereby the needle will be positioned within the cavity with its tip inaccessible to inadvertent contact when the wing engages the transverse enlargement.

13. A method of preventing inadvertent contact with the tip of a needle of a needle administration set after completion of a medical procedure, the administration set comprising a needle assembly and a length of tubing, the needle assembly including a needle having a tip at one end and a coaxial base, the base being connected to the needle at the opposite end, the base including at least one laterally projecting wing and one end of the tubing being connected to the base, the method including the steps of:
 (a) threading the other end of the tubing through a generally cylindrical sleeve having at least a portion with a rigid obstruction comprising a maximum dimension transverse to the longitudinal axis of the sleeve which is less than the radial length of the wing,
 (b) moving the needle assembly toward the sleeve,
 (c) deforming the wing to reduce its radial length and positioning the base and wing in the sleeve and in registry with the obstruction,
 (d) continuing to move the needle assembly relative to the sleeve until the tip of the needle is inaccessibly positioned within the sleeve, and
 (e) locking the needle assembly within the sleeve by registering the wing with an unobstructed portion of the sleeve and permitting the wing to expand its radial length.

14. A method of preventing inadvertent contact with the tip of a needle of a needle administration set in accordance with claim 13 wherein the needle assembly is moved relative to the sleeve by pulling the tubing relative to the sleeve.

15. A method of preventing inadvertent contact with the tip of a needle of a needle administration set in accordance with claim 13 wherein the step of deforming the wing includes the step of spirally wrapping the wing about the longitudinal axis of the base.

16. A method of preventing inadvertent contact with the tip of a needle of a needle administration set in accordance with claim 15 wherein the sleeve includes an outwardly flared opening facing the needle assembly during the medical procedure, the step of deforming the wing including pulling the tubing relative to the sleeve and engaging the wing against the outwardly flared opening.

17. A method of preventing inadvertent contact with the tip of a needle of a needle administration set after completion of a medical procedure, the administration set comprising a needle assembly and a length of tubing, the needle assembly including a needle having a tip at one end and a coaxial base, the base being connected to the needle at the opposite end, the base including at least one laterally projecting wing and one end of the tubing being connected to the base, the method including the steps of:
 (a) providing a puncture guard constructed in accordance with claim 1;
 (b) threading the length of tubing through the cavity with the one end opening facing the needle assembly;
 (c) urging the needle assembly toward the cavity by pulling the tubing relative to the body;
 (d) radially compressing the wing by bending the wing in a spiral configuration to permit entry of the base into the portion of the cavity; and (e) locking the needle assembly within the cavity by registering the wing with the transverse opening and expanding the wing to its undeformed radial length through the transverse opening.

18. A method of preventing inadvertent contact with the tip of a needle of a needle administration set as set forth in claim 17 wherein a portion of the body is outwardly flared at the one end opening, the step of radially compressing including engaging the wing with the flared portion of the body while continuing the step of moving the tubing relative to the body.

19. A method of preventing inadvertent contact with the tip of a needle of a needle administration set as set forth in claim 18 wherein the step of radially compressing includes simultaneously rotating the body relative to the needle assembly while continuing the step of moving the tubing relative to the body.

20. A method of preventing inadvertent contact with the tip of a needle of a needle administration set as set forth in claim 17 wherein the step of locking includes rotating the body relative to the needle assembly when the wing is registered with the transverse opening.

21. A method of preventing inadvertent contact with the tip of a needle of a needle administration set as set forth in claim 17 wherein the base of the needle assembly includes a pair of wings, the step of locking including expanding both wings through the transverse opening.

* * * * *